(12) United States Patent
Safari

(10) Patent No.: US 9,351,522 B2
(45) Date of Patent: May 31, 2016

(54) CARTOMIZER E-CIGARETTE

(71) Applicant: Robert Safari, San Jose, CA (US)

(72) Inventor: Robert Safari, San Jose, CA (US)

( * ) Notice: Subject to any disclaimer, the term of this patent is extended or adjusted under 35 U.S.C. 154(b) by 842 days.

(21) Appl. No.: 13/629,541

(22) Filed: Sep. 27, 2012

(65) Prior Publication Data

US 2013/0081642 A1  Apr. 4, 2013

Related U.S. Application Data

(60) Provisional application No. 61/541,039, filed on Sep. 29, 2011.

(51) Int. Cl.
*A24F 47/00* (2006.01)
*A61M 15/06* (2006.01)

(52) U.S. Cl.
CPC .............. *A24F 47/008* (2013.01); *A24F 47/002* (2013.01); *A61M 15/06* (2013.01)

(58) Field of Classification Search
CPC ..... A24F 47/00; A24F 47/002; A24F 47/004; A24F 47/008; A61M 15/06
See application file for complete search history.

(56) References Cited

U.S. PATENT DOCUMENTS

| | | | |
|---|---|---|---|
| 6,155,268 A * | 12/2000 | Takeuchi | A24F 47/008 131/194 |
| 6,443,146 B1 | 9/2002 | Voges | |
| 6,532,965 B1 | 3/2003 | Abhulimen | |
| 7,832,410 B2 | 11/2010 | Hon | |
| 2005/0016550 A1 | 1/2005 | Katase | |
| 2011/0094523 A1* | 4/2011 | Thorens | A24F 47/008 131/194 |
| 2012/0145169 A1* | 6/2012 | Wu | A24F 47/008 131/273 |
| 2012/0199146 A1 | 8/2012 | Marangos | |
| 2013/0228191 A1* | 9/2013 | Newton | A24F 47/008 131/329 |

* cited by examiner

*Primary Examiner* — Anthony Calandra
(74) *Attorney, Agent, or Firm* — P. J. Benedict O'Mahoney

(57) ABSTRACT

An electronic cigarette with a battery unit and a cartomizer unit which includes a cartomizer component which integrates a liquid chamber for receiving a liquid solution and an atomization chamber disposed adjacent to the liquid chamber and separated therefrom by a dividing wall, the dividing wall having a dividing wall opening formed therein, and a guiding wick that extends through the dividing wall opening from the liquid chamber to the atomization chamber to supply liquid solution from the liquid chamber to the atomization chamber.

16 Claims, 5 Drawing Sheets

CARTOMIZER E-CIGARETTE

CROSS-REFERENCE TO RELATED APPLICATIONS

The present application claims the benefit of U.S. Provisional Application No. 61/541,039, filed Sep. 29, 2011, by Robert Safari and titled "Cartomizer E-Cigarette", included by reference herein and for which benefit of the priority date is hereby claimed.

FEDERALLY SPONSORED RESEARCH

Not applicable.

SEQUENCE LISTING OR PROGRAM

Not applicable.

FIELD OF INVENTION

The present invention relates to electronic cigarettes (e-cigarettes) and, in particular, to a cartomizer e-cigarette in which a battery unit is connected to a cartomizer unit which includes a liquid chamber, an atomization chamber and a guiding wick that provides liquid solution from the liquid chamber to the atomization chamber.

BACKGROUND OF THE INVENTION

An electronic cigarette, or e-cigarette, is an electronic device that simulates the act of tobacco smoking by producing an inhaled mist or aerosol bearing the physical sensation, appearance, and the flavor and nicotine of inhaled tobacco smoke, without the odor and health risks associated with tobacco cigarettes. An e-cigarette generally uses heat or ultrasonics to vaporize a propylene glycol- or glycerin-based liquid solution into an aerosol for inhalation.

E-cigarettes are portable, self-contained cylindrical devices the size of which depends upon battery capacity. E-cigarettes have been designed to resemble actual cigarettes, cigars or even pipes. Some e-cigarettes are reusable, with replaceable and refillable parts; others are disposable.

E-cigarettes share three essential components. A "cartridge" serves as a mouthpiece and usually doubles as a small reservoir that holds the liquid that is to be vaporized. An atomizer serves as the heating element responsible for vaporizing the liquid to provide the aerosol mist. A battery unit serves as a battery supply in portable e-cigarette models. Other electronic components necessary for e-cigarette operation are housed within the battery unit.

A "cartomizer" option is available for many e-cigarettes. The cartomizer replaces the separate cartridge and atomizer components with a single integrated component, hence the nomenclature "cartomizer." The cartomizer is disposable, as opposed to stand-alone atomizers that are reusable and comparatively expensive.

The cartridge is a small, usually disposable plastic container, with openings on each end. One end is placed in the user's mouth; the other end attaches to the atomizer. The cartridge serves as both a liquid reservoir and mouthpiece, and as such, must allow the passage of liquid to the atomizer, as well as aerosol from the atomizer back to the user's mouth without allowing liquid into the mouth. This is usually accomplished using an absorbent sponge-like material placed in the cartridge to keep the liquid in place and which rests on a plastic barrier separating it from the mouthpiece opening.

The mouthpiece casing is constructed with side channels that allow aerosol mist to pass from the atomizer, around the liquid reservoir, to the mouthpiece opening and, thus, into the user's mouth. When the liquid in the cartridge has been depleted, the user can usually chose between refilling it or replacing it with another pre-filled cartridge.

The atomizer is a heating element that is responsible for vaporizing the liquid solution. The atomizer typically includes a simple filament and metal mesh to draw the liquid solution in from the cartridge. The atomizer is positioned in the center of the three components. That is, the cartridge attaches to one end of the atomizer and the battery unit attaches to the other end of the atomizer. The atomizer's filament tends to lose efficiency over time due to a build-up of sediment, or burns out entirely, requiring replacement.

Most portable e-cigarette battery units contain a rechargeable lithium-ion battery. The housing for the battery and the electronic circuitry required for operation of the e-cigarette is usually the largest component of the e-cigarette. The battery unit typically contains an electronic airflow sensor so that activation of the e-cigarette is triggered by drawing breath through the device. A colored LED may also be included in the battery unit to announce activation of the e-cigarette.

The contents of the liquid solution used to produce aerosol mist in e-cigarettes vary widely, but their common aspects include water and flavorings (e.g., tobacco smoke) in a propylene glycol or glycerin base. Nicotine is also included in solutions intended to fulfill a nicotine replacement role, without the carcinogenic tar associated with tobacco smoke.

U.S. Pat. No. 7,832,410, which issued on Nov. 16, 2010, discloses an example of an electronic atomization cigarette. U.S. Pat. No. 7,832,410 is hereby incorporated by reference herein in its entirety to provide background information regarding the present invention.

SUMMARY OF THE INVENTION

An embodiment of the invention provides a cartomizer unit for use in an electronic cigarette. The cartomizer unit includes a liquid chamber for receiving a liquid solution, an atomization chamber disposed adjacent to the liquid chamber and separated therefrom by a dividing wall, the dividing wall having a dividing wall opening formed therein, and a guiding wick that extends through the dividing wall opening from the liquid chamber to the atomization chamber to supply liquid solution from the liquid chamber to the atomization chamber.

The features and advantages of the present invention will be more fully understood and appreciated upon consideration of the following detailed description and accompanying drawings, which set forth illustrative embodiments in which the concepts of the invention are utilized.

BRIEF DESCRIPTION OF THE DRAWINGS

A complete understanding of the present invention may be obtained by reference to the accompanying drawings, when considered in conjunction with the subsequent, detailed description, in which.

DETAILED DESCRIPTION

Before the invention is described in further detail, it is to be understood that the invention is not limited to the particular embodiments described, as such may, of course, vary. It is also to be understood that the terminology used herein is for the purpose of describing particular embodiments only, and not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed with the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context clearly dictates otherwise.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, if dates of publication are provided, they may be different from the actual publication dates and may need to be confirmed independently.

Figure 1:
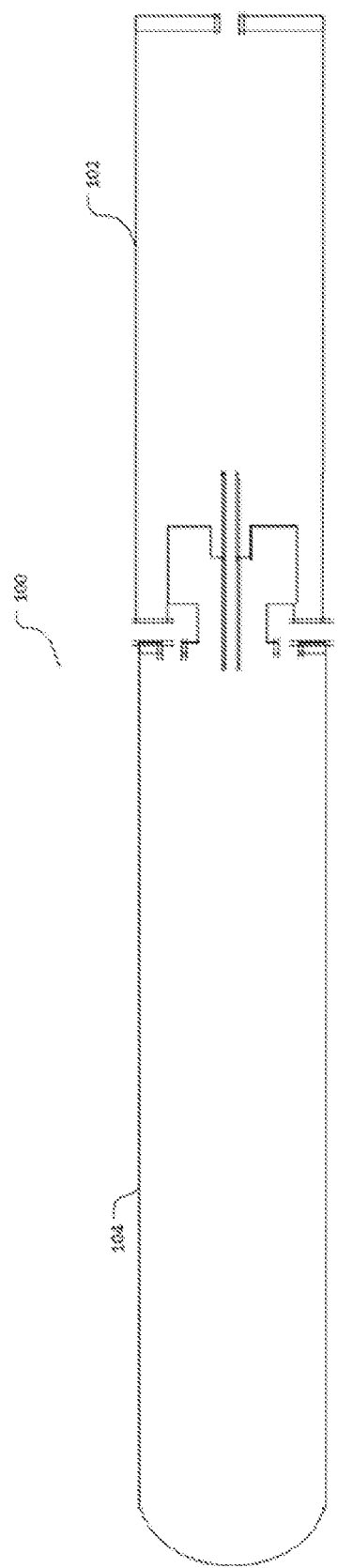
FIG. 1 is a drawing illustrating an embodiment of a cartomizer e-cigarette in accordance with the concepts of the present invention comprising a battery unit connected to a cartomizer unit.

FIG. 1 generally shows an embodiment of a cartomizer e-cigarette 100. The cartomizer e-cigarette 100 includes a cartomizer unit 102 and a battery unit 104 that attaches to the cartomizer unit 102, as described in greater detail below.

Figure 2:
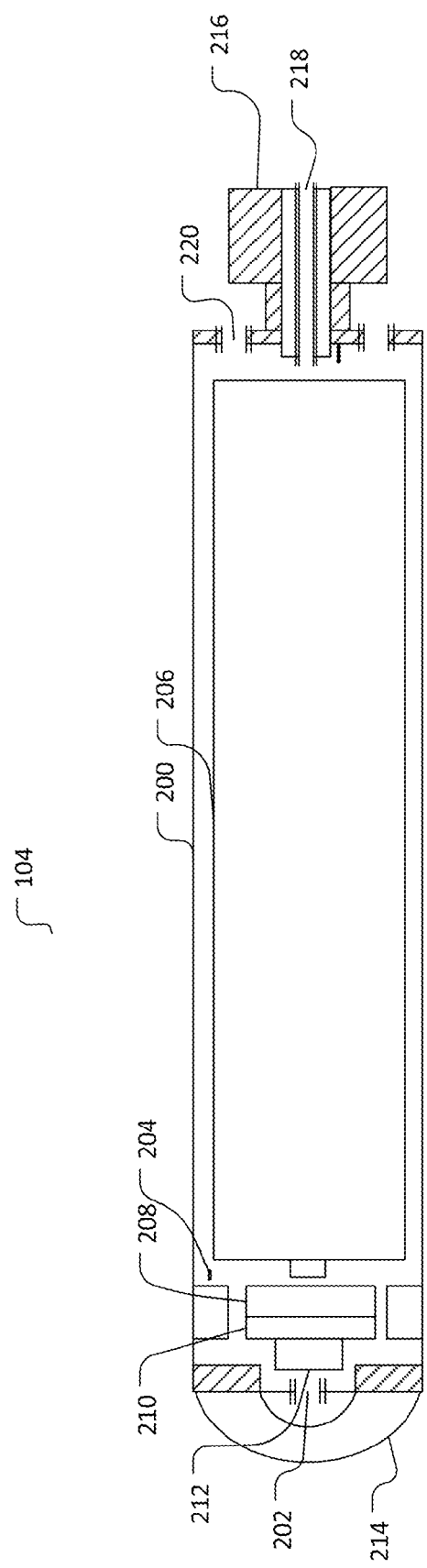
FIG. 2 is a drawing illustrating the battery unit shown in FIG. 1.

Turning now to FIG. 2, the battery unit 104 is shown in detail and separated from the cartomizer unit 102. The battery unit 104 is disposed within a cylindrical battery unit tube 200 to provide a battery unit annular space 204 between an inside wall of the battery unit tube 200 and the battery 206. In one embodiment, the cylindrical battery unit tube 200 is made from a metal to provide a durable product. In another embodiment, the cylindrical battery unit tube 200 is made from a plastic material to provide a more light weight product that more closely mimics the experience of a real cigarette. In the illustrated embodiment, the battery unit 104 has one or more battery unit air intake openings 202 formed near the "lighted" end of the e-cigarette 100. The one or more battery unit air intake openings 202 are in air flow communication with the battery unit annular space 204. The battery unit 104 includes a battery (e.g., a rechargeable lithium-ion battery) 206 that is electrically connected to switch controller circuitry 208. Switch controller circuitry 208 provides an activation signal to the heating element in the cartomizer unit 104 as discussed hereunder. A pressure sensor 210 is connected to the switch controller circuitry 208 and is in air flow communication with the one or more battery unit air intake openings 202. The pressure sensor 210 responds to an air pressure change stimulus by causing the switch controller circuitry 208 to provide the activation signal to the heating element in the cartomizer unit 104.

In the illustrated embodiment, a light emitting diode (LED) 212 is communicatively connected to the switch controller circuitry 208. A light cap 214 fits into an open end of the battery unit tube 200. The light cap 214 may be translucent and tinted so that, when the LED 212 is illuminated in response to the activation signal received from the switch controller circuitry 208, the light cap 214 simulates the burning end of a lit tobacco cigarette. Battery units of the type described above are commercially available from Desay Polypower Battery Co., Ltd. located in Guangdong, China.

In the illustrated embodiment, a second threaded male brass fitting 216 is disposed at a second end of the battery tube 200. The second fitting 216 has an axial second air flow opening 218 formed therein. The second fitting 216 further includes one or more second fitting air intake openings 220 formed therein to provide air flow communication through the second fitting 216 to the battery unit annular space 204. The second fitting 216 is adapted for sealing connection to the first fitting of the cartomizer unit 104 such that the axial second fitting air flow opening 218 aligns with the axial first fitting air flow opening of the cartomizer unit 104 to provide air flow communication between the battery unit annular space 204 and the cartomizer annular space in the cartomizer unit 104, as more fully described below.

Figure 3:
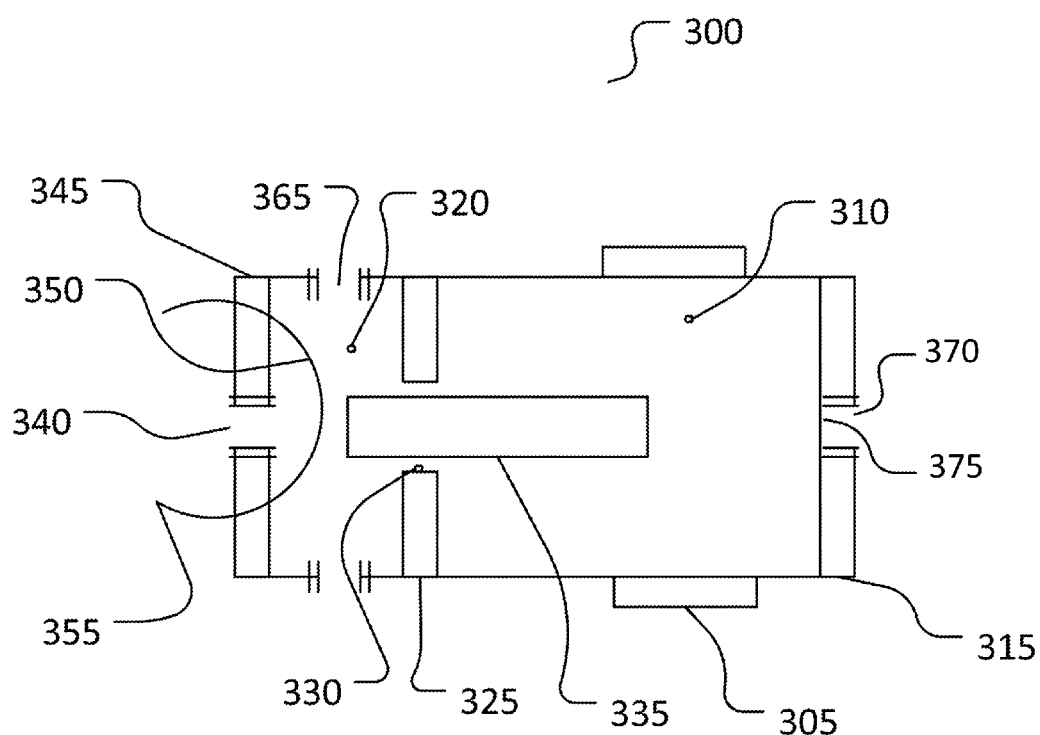
FIG. 3 is an enlarged drawing illustrating the cartomizer component which is part of the cartomizer unit shown in FIG. 1.

Turning now to FIG. 3, the cartomizer component 300 of the cartomizer unit 104 is shown in detail. In the illustrated embodiment, the cartomizer component 300 includes a liquid chamber 310 that contains a liquid solution. In some embodiments, the liquid chamber 310 is refillable by removing the liquid chamber end cap 315 and introducing new liquid solution to the liquid chamber 310. In other embodiments, the liquid chamber end cap 315 may be configured with an air intake opening 370 covered with a semi-permeable membrane 375 allowing air into the liquid chamber while retain the liquid solution within the liquid chamber. In other embodiments, the liquid chamber 310 may be sealed. In either case, the cartomizer component 300 may be removable and may be replaced with a new cartomizer component 300 that contains new liquid solution in the liquid chamber 310. The liquid solution in the replacement cartomizer component 300 may be the same as or different than the liquid solution contained in the previous cartomizer component 300. The liquid solution typically is a propylene glycol- or glycerin-based solution of the type well known to those skilled in the art. The liquid solution typically includes a flavoring, e.g., tobacco, and may also include nicotine, as is also well known to those skilled in the art.

In the illustrated embodiment, the cartomizer component 300 further includes an atomization chamber 320 disposed adjacent to the liquid chamber 310 and separated therefrom by a dividing wall 325 that has a dividing wall opening 330 formed therein. A guiding wick 335, e.g., a cotton wick, extends through the dividing wall opening 330 from the liquid chamber 310 to the atomization chamber 320 to supply liquid solution from the liquid chamber 310 to the atomization chamber 320. In the illustrated embodiment, an atomization chamber air intake opening 340 is formed in an end wall 345 of the atomization chamber 320. In one embodiment of the invention, the atomization chamber air intake opening 340 is an oval shape and disposed diagonally in the end wall 345. Those skilled in the art will appreciate that one or more air intake openings may be formed in the walls of the atomization chamber 320. The atomization chamber 320 also has one or more vapor exit openings 365 formed therein to provide liquid solution aerosol mist communication between the atomization chamber 320 and the cartomizer unit annular space, as discussed in greater detail below.

A heating element 350 is disposed within the atomization chamber 320 in proximity to the guiding wick 335. In the illustrated embodiment, the heating element 350 comprises a simple wire coil filament that is wrapped around a cylindrical insulating core. The heating element 350 responds to an activation signal by vaporizing the liquid solution supplied to the atomization chamber 320 to provide liquid solution aerosol mist.

Figure 4:
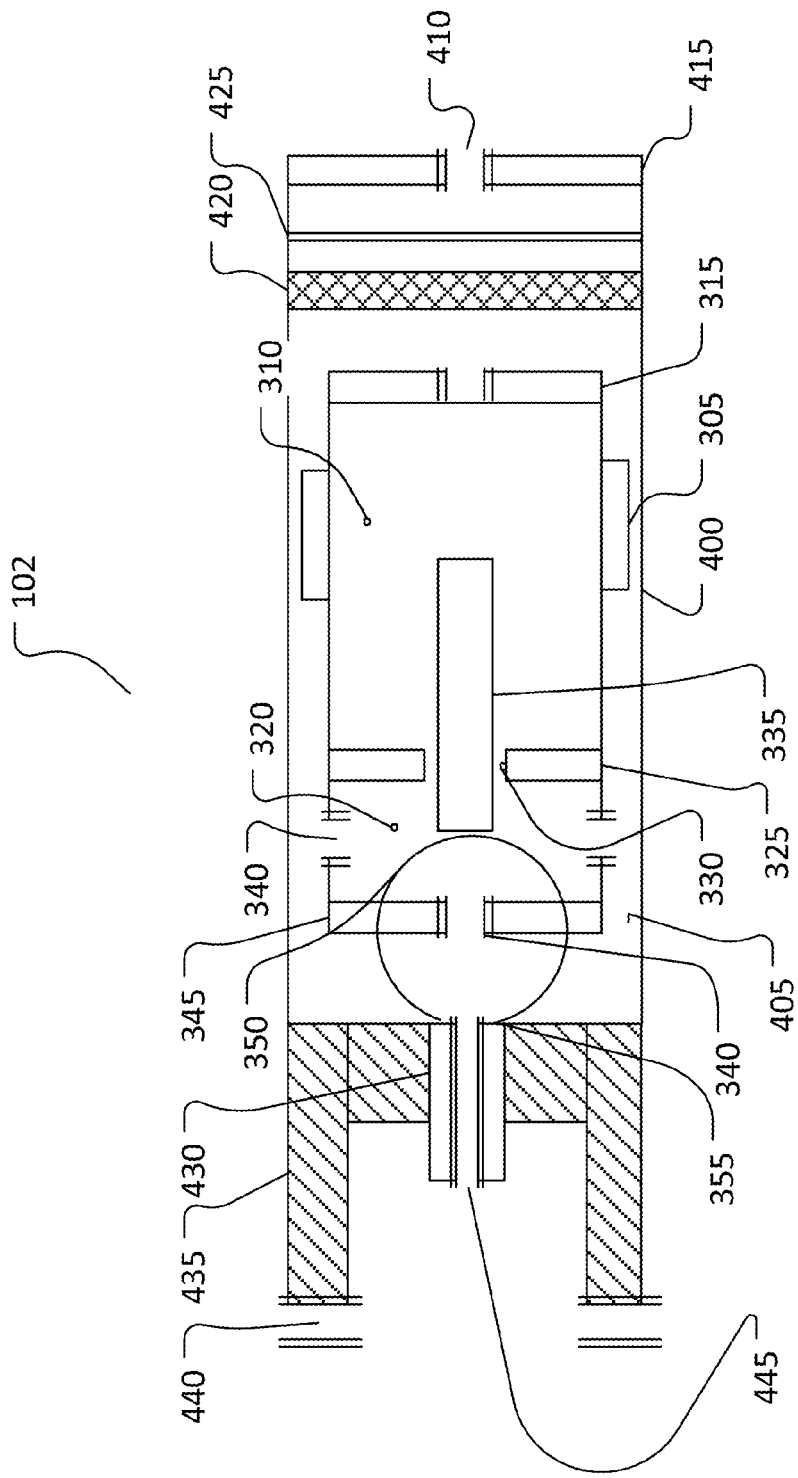
FIG. 4 is a drawing illustrating the cartomizer unit shown in FIG. 1.

Turning now to FIG. 4, the cartomizer component 300 is shown disposed in the cartomizer unit 102. The generally cylindrical cartomizer component 300 is disposed within a cylindrical mouthpiece tube 400. In one embodiment, the cylindrical mouthpiece tube 400 is made from a metal to provide a durable product. In another embodiment, the cylindrical mouthpiece tube 400 is made from a plastic material to provide a more light weight product that more closely mimics the experience of a real cigarette. The cartomizer component 300 is of lesser diameter than the mouthpiece tube 400 so as to provide a cartomizer unit annular space 405 between the inside wall of the mouthpiece tube 400 and the outside wall of the cartomizer unit 102. In some embodiments, a plurality of spaced apart ribs 305 are formed on the outside wall of the cartomizer component 300 to provide stability to the cartomizer component 300 within the mouthpiece tube 400 while still permitting air flow in the cartomizer unit annular space 405. The mouthpiece tube 400 has a draw opening 410 formed in it so that a user can apply the inhale portion of the user's breath to the cartomizer unit annular space 405. In the illustrated embodiment, a draw end cap 415, e.g., a plastic cap, covers the draw end of the cylindrical mouthpiece tube 400 except for the axially located draw opening 410 formed through the cap 415.

The illustrated embodiment also includes a metal mesh pad 420 and a porous vinyl foam pad 425 disposed within the mouthpiece tube 400 between the liquid chamber 310 and the draw end of the mouthpiece tube 400. Both the metal mesh pad 420 and the vinyl foam pad 425 are circular in shape and of approximately the same diameter as the inner wall of the mouthpiece tube 400. The metal mesh pad 420 and the vinyl foam pad 425 remove liquid solution droplets that may exist within the aerosol mist passing from the cartomizer unit annular space 405 to the draw opening 410 to prevent the liquid solution droplets from reaching the user's mouth during a user inhale.

As discussed above, the illustrated cartomizer unit 102 is, in keeping with the cylindrical shape of the e-cigarette 100, a generally cylindrical unitary structure that may be formed in a variety of physical formations and may be formed by any suitable technique well known to those skilled in the art, including encapsulation techniques. The cartomizer component 300 may be made of any suitable material well known to those skilled in the art, such as those used for drug delivery, liquid encapsulated capsules, or other encapsulation materials. Single wall or multi-wall structures may be used to tailor stability, strength and rupture resistance of the cartomizer component 300.

In the illustrated embodiment, a first threaded female brass fitting 435 is disposed at a second end of the mouthpiece tube 400. The first fitting 435 has an axial air flow opening 445 formed therein to enable air flow through the first fitting 435 to the cartomizer unit annular space 405. The first fitting 435 also includes one or more first fitting air intake openings 440 formed at the end of the threaded portion of the first fitting 435.

Figure 5:
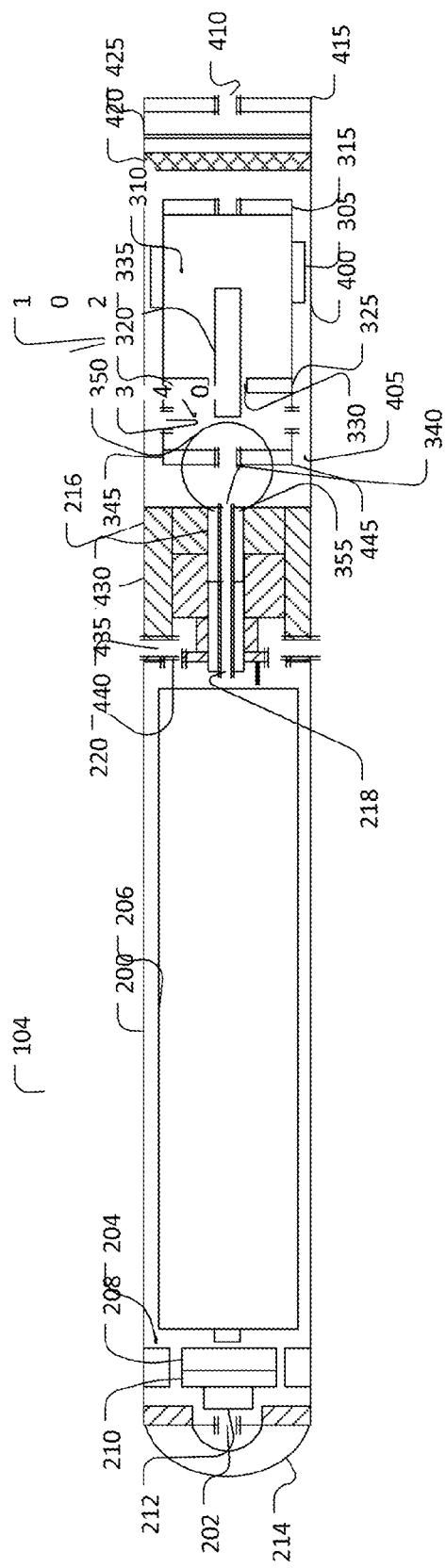
FIG. 5 is a drawing illustrating the FIG. 1 embodiment in more detail of a cartomizer e-cigarette wherein the cartomizer unit is connected to the battery unit to provide a unitary cartomizer e-cigarette device.

FIG. 5 shows the sealed connection of the cartomizer unit 102 and the battery unit 104 by the threaded engagement of the male fitting 216 of the battery unit 104 with the female fitting 435 of the cartomizer unit 102 to provide the unitary structure of the cartomizer e-cigarette 100. FIG. 5 further shows that, when the first and second fittings are connected, the one or more first fitting air intake openings 440 are in air flow communication with the one or more second fitting air intake openings 220 to provide air intake flow to the battery unit annular space 204.

With reference to FIG. 5, when a user applies an inhale portion of the user's breath to the mouthpiece end of the cartomizer unit 102, the pressure sensor 210 senses a pressure change in the interior of the e-cigarette 100 and causes the switch controller circuitry 208 to activate the heating element 350 by applying a current from the electronically connected battery 206, thereby producing a liquid solution aerosol mist in the atomization chamber 320. The user's inhale also causes air intake at the first fitting air intake openings 440, which is passed through the second fitting air intake openings 220, through the axial second air flow opening 218 and axial first air flow opening 445 in the second fitting 216 and first fitting 435, respectively, to combine with the liquid solution aerosol mist formed in the atomization chamber 320 and pass through cartomizer unit annular space 405 and the draw end opening 410 into the user's mouth. At the same time, air flow passes through the battery unit air intake openings 202, through the battery unit annular space 204 and the axial second air flow opening 218 and axial first air flow opening 445 in the second fitting 216 and first fitting 435, respectively, to also combine with the liquid solution aerosol mist flowing to the user's mouth through the draw opening 410.

It should be further understood that the examples and embodiments pertaining to the systems and methods disclosed herein are not meant to limit the possible implementations of the present technology. Further, although the subject matter has been described in a language specific to structural features and/or methodological acts, it is to be understood that the subject matter defined in the appended claims is not necessarily limited to the specific features or acts described above. Rather, the specific features and acts described above are disclosed as example forms of implementing the Claims.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

What is claimed is:

1. A cartomizer unit for use in an electronic cigarette, the cartomizer unit comprising:
   a liquid chamber for receiving a liquid solution, wherein the liquid chamber includes a liquid chamber end cap that is removable for allowing the liquid solution to be received by the liquid chamber and an air intake opening formed therein wherein said air intake opening is covered with a semi-permeable membrane allowing air into the liquid chamber while retaining the liquid solution with the liquid chamber;
   an atomization chamber disposed adjacent to the liquid chamber and separated therefrom by a dividing wall, the dividing wall having a dividing wall opening formed therein;
   at least one atomization chamber vent formed in the atomization chamber for receiving air and expelling a liquid solution aerosol mist; and
   a guiding wick that extends through the dividing wall opening from the liquid chamber to the atomization chamber to supply liquid solution from the liquid chamber to the atomization chamber.

2. The cartomizer unit of claim 1, wherein the guiding wick comprises cotton.

3. The cartomizer unit of claim 1, further comprising:
   a heating element disposed within the atomization chamber in proximity to the guiding wick for vaporizing the liquid solution supplied to the atomization chamber to provide a liquid solution aerosol mist.

4. The cartomizer unit of claim 3, further comprising an atomization chamber end cap with the heating element attached thereto such that the heating element is disposed within the atomization chamber and heating element terminals are disposed outside of the atomization chamber.

5. The cartomizer unit of claim 4, wherein the liquid chamber and the atomization chamber are disposed within a cylindrical mouthpiece tube wherein the end of said cylindrical mouthpiece tube adjacent to the liquid chamber is capped with a draw end cap and the end of said cylindrical mouthpiece tube adjacent to the atomization chamber is capped with a first fitting.

6. The cartomizer unit of claim 5, further comprising at least one rib attached to the outer wall of the atomization chamber or liquid chamber providing cartomizer unit annular space between the wall of the cylindrical mouthpiece tube and the atomization chamber and liquid chamber.

7. The cartomizer unit of claim 5, wherein the first fitting comprises an outer threaded fitting surrounding a cylindrical insulating core surrounding a heating element contact surrounding an axial air flow opening.

8. The cartomizer unit of claim 6, wherein the heating element terminals are connected to the heating element contact.

9. The cartomizer unit of claim 6, further comprising at least one first fitting air intake opening formed therein.

10. An electronic cigarette comprising:
    a cartomizer unit comprising
        a liquid chamber that contains a liquid solution, wherein the liquid chamber includes a liquid chamber end cap that is removable for allowing the liquid solution to be received by the liquid chamber and an air intake opening formed therein wherein said air intake opening is covered with a semi-permeable membrane allowing air into the liquid chamber while retaining the liquid solution with the liquid chamber;
        an atomization chamber disposed adjacent to the liquid chamber and separated therefrom by a dividing wall, the dividing wall having a dividing wall opening formed therein, and
        a guiding wick that extends through the dividing wall opening from the liquid chamber to the atomization chamber to supply liquid solution from the liquid chamber to the atomization chamber; and
    a power unit connected to the cartomizer unit.

11. The electronic cigarette of claim 10, further comprising:
    a heating element disposed within the atomization chamber in proximity to the guiding wick for vaporizing the liquid solution supplied to the atomization chamber to provide a liquid solution aerosol mist.

12. The electronic cigarette of claim 10, wherein the liquid solution comprises a propylene glycol-based liquid solution.

13. The electronic cigarette of claim 10, wherein the liquid solution includes nicotine.

14. The electronic cigarette of claim 11, wherein the battery unit includes:
    a battery;
    switch controller circuitry connected to the battery configured to provide an activation signal to the heating element that causes the heating element to generate heat that vaporizes the liquid solution supplied to the atomization chamber to provide the liquid solution aerosol mist; and
    a pressure sensor communicatively connected to the switch controller circuitry wherein the pressure sensor responds to a stimulus by causing the switch controller circuitry to provide the activation signal to the heating element.

15. An electronic cigarette comprising:
    a mouthpiece tube having a mouthpiece opening formed in a draw end of the mouthpiece tube;
    a cartomizer unit disposed within the mouthpiece tube to provide a cartomizer unit annular space between an inside wall of the mouthpiece tube and the cartomizer unit, the cartomizer unit including
        (i) a liquid chamber that contains a liquid solution, wherein the liquid chamber includes a liquid chamber end cap that is removable for allowing the liquid solution to be received by the liquid chamber and an air intake opening formed therein wherein said air intake opening is covered with a semi-permeable membrane allowing air into the liquid chamber while retaining the liquid solution with the liquid chamber;
        (ii) an atomization chamber disposed adjacent to the liquid chamber and separated therefrom by a dividing wall, the dividing wall having a dividing wall opening formed therein, the atomization chamber having one or more atomization chamber air intake openings formed therein, the atomization chamber further having one or more aerosol mist exit openings formed therein to provide liquid solution vapor mist communication between the atomization chamber and the cartomizer unit annular space; and
        (iii) a guiding wick that extends through the dividing wall opening from the liquid chamber to the atomization chamber to supply liquid solution from the liquid chamber to the atomization chamber;
        (iv) a heating element disposed within the atomization chamber in proximity to the guiding wick, the heating element responding to an activation signal by vaporizing the liquid solution supplied to the atomization chamber to provide liquid solution aerosol mist;

a first fitting disposed at a second end of the mouthpiece tube opposite the first end of the mouthpiece tube, the first fitting having an axial first fitting air flow opening formed therein to enable air flow through the first fitting to the cartomizer unit annular space;

a battery unit tube having one or more battery unit air intake openings formed therein;

a battery unit disposed within the battery unit tube to provide a battery unit annular space between an inside wall of the battery unit tube and the battery unit, the battery unit including
 (i) a battery;
 (ii) switch controller circuitry connected to the battery and that provides an activation signal to the heating element to generate heat that causes the heating element to vaporize the liquid solution in the atomization chamber to provide the liquid solution aerosol mist;
 (iii) a pressure sensor connected to the switch controller circuitry and in air flow communication with the one or more battery unit air intake openings such that the pressure sensor responds to an air pressure change stimulus by causing the switch controller circuitry to provide the activation signal to the heating element; and a second fitting disposed at a first end of the battery unit tube, the second fitting having an axial second fitting air flow opening formed therein, the second fitting being adapted for sealing connection to the first fitting such that the axial second fitting air flow opening is aligned with the axial first fitting air flow opening to provide air flow communication between the battery unit annular space and the cartomizer unit annular space.

16. The electronic cigarette of claim 15, wherein the first fitting further comprises one or more first fitting air intake openings formed therein, and wherein the second fitting further comprises one or more second fitting air intake openings formed therein, the second fitting being adapted for sealing connection to the first fitting such that the one or more first fitting air intake openings are in air flow communication with the one or more second fitting air intake openings to provide air intake flow to the battery unit annular space.

* * * * *